United States Patent [19]

Kanojia et al.

[11] Patent Number: 4,880,817

[45] Date of Patent: * Nov. 14, 1989

[54] O-FUNCTIONALIZED DERIVATIVES OF SUBSTITUTED ISOQUINOLIN-3-OLS HAVING CARDIOTONIC AND/OR PHOSPHODIESTERASE FRACTION III INHIBITING PROPERTIES AND/OR RENAL VASODILATING PROPERTIES

[75] Inventors: Ramesh M. Kanojia, Somerville; O. William Lever, Jr., Skillman; Jeffery B. Press, Rocky Hill, all of N.J.

[73] Assignee: Ortho Pharmaceutical Corporation, Raritan, N.J.

[*] Notice: The portion of the term of this patent subsequent to Dec. 22, 2005 has been disclaimed.

[21] Appl. No.: 59,699

[22] Filed: Jun. 9, 1987

[51] Int. Cl.$^4$ .................. A61K 31/47; C07D 217/24
[52] U.S. Cl. ............................ 514/309; 514/210;
514/235.2; 514/253; 544/128; 544/363;
546/141
[58] Field of Search ............ 546/141; 514/309, 235.2,
514/210, 253; 544/128, 363; 540/597

[56] References Cited

U.S. PATENT DOCUMENTS 3,798,225 3/1974 Kreighbaum et al. ............... 546/141
4,409,017 10/1983 Serban et al. ........................ 546/141
4,714,705 12/1987 Kanojia et al. ...................... 546/141

OTHER PUBLICATIONS

Deak, et al., "Chemical Abstracts", vol. 80, 1973, Col. 27075s.
Sanders, et al., (I), "Chemical Abstracts", vol. 84, 1976, Col. 135439e.
Kasturi, et al., (I), "Chemical Abstracts", vol. 87, 1977, Col. 53049a.
Muro, et al., "Chemical Abstracts", vol. 88, 1978, Col. 152448g.
Sanders, et al., (II), "Chemical Abstracts", vol. 89, 1978, Col. 42116k.
Kasturi, et al., (II), "Chemical Abstracts", vol. 93, 1980, Col. 93:114296b.
VanVeldhuizen, et al., "Chemical Abstracts", vol. 94, 1980, Col. 94:14651r.
Knyazeva, et al., "Chemical Abstracts", vol. 95, 1981, Col. 95:115235j.
Krishman, et al., "Chemical Abstracts", vol. 96, 1982, Col. 96:181116t.
Sindler-Kulyk, et al., "Chemical Abstracts", vol. 98, 1983, Col. 98:160626k.
Hazai, et al., "Chemical Abstracts", vol. 101, 1984, Col. 101:210946t.
Win, et al., "Jour. Org. Chem.", vol. 32, 1967, pp. 59–61.

Primary Examiner—Glennon H. Hollrah
Assistant Examiner—James H. Turnipseed
Attorney, Agent, or Firm—Benjamin F. Lambert

[57] ABSTRACT

O-functional derivatives of substituted isoquinolin-3-ol compounds of the general formula

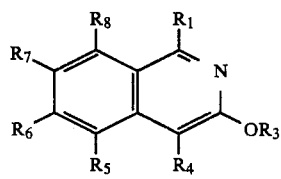

that exhibit cardiotonic and/or phosphodiesterase fraction III inhibiting properties and/or renal vasodilating are pharmacologically active in the treatment of cardiac conditions. Methods for synthesizing and using the compounds are described.

15 Claims, No Drawings

O-FUNCTIONALIZED DERIVATIVES OF SUBSTITUTED ISOQUINOLIN-3-OLS HAVING CARDIOTONIC AND/OR PHOSPHODIESTERASE FRACTION III INHIBITING PROPERTIES AND/OR RENAL VASODILATING PROPERTIES

DESCRIPTION

1. Technical Field

The present invention relates to O-functionalized derivatives of 4-substituted isoquinolin-3-ol compounds that exhibit cardiotonic properties and/or phosphodiesterase fraction III inhibiting properties and/or renal vasodilating properties, as well as methods for synthesis and utility of these compounds.

2. Background

Compounds that exhibit cardiotonic properties cause cardiac muscle to pump more forcefully and effectively (a positive inotropic effect) and are often used to treat heart failure. Digitalis is one of the most frequently used cardiotonic agents; other examples include ouabain and strophanthidin.

Vasodilating agents produce a relaxation of the muscles of blood vessels that correspondingly enlarges the blood vessel passage, reduces resistance to blood flow and lowers blood pressure. As a result, more blood reaches the tissues. Examples of such agents include nitroglycerin, other nitrates, hydralazine and the like. Renal vasodilators produce a relaxation of blood vessels that are associated with the kidneys.

Phosphodiesterases convert c-AMP (cyclic adenosine monophosphate) to 5′-AMP. Cardiac phosphodiesterase fraction III is one example of a biologically active phosphodiesterase. Compounds that inhibit phosphodiesterase activity and its breakdown of cAMP therefore provide enhanced levels of cAMP.

A number of compounds that are structurally related to isoquinolines and isoquinolinols have been described in the literature.

U.S. Pat. Nos. 3,798,225, 3,910,927 and 4,015,006 to Kreighbaum et al. (Mead Johnson & Co.) relate to 2-substituted-3(2H)-isoquinolones and 2-substituted-3-alkoxyisoquinolines that are reported to have hypotensive and peripheral vasodilating properties upon oral administration. The patents relate in particular to 1-benzyl derivatives of the above compounds.

The preparation of 3-hydroxy-6,7-dimethoxy-1-methylisoquinoline and the corresponding tautomeric form, 6,7-dimethoxy-1-methyl-3(2H)-isoquinolone, which is the parent compound of several compounds of this invention, has been reported along with the preparation of the corresponding 3-ethoxy and 3-acetoxy derivatives [Bentley et al., *J. Chem. Soc.*, 1763 (1952); Dorofeenko et al., *USSR Author's certificate No.* 207,921, CA, 69, 52003x (1967); and D. Evans et al., *J. Chem. Soc. (B)*, 590 (1967)].

The 4-substituted isoquinolin-3-ol compounds used as starting materials in this invention are prepared according to the procedure described in our copending applications Ser. No. 871,967 filed June 9, 1986 now U.S. Pat. No. 4,822,800 and Ser. No. 882,655 filed July 7, 1986 now U.S. Pat. No. 4,714,705, all of said procedures being incorporated herein by reference.

1-Phenylisoquinoline derivatives are described in German Offenlegunschrift DE-3,227,741 which issued to Hoechst AG. The compounds are reported to exhibit antidepressant activity. U.S. Pat. Nos. 4,282,222 and 4,282,223 to Bartmann et al. (assigned to Hoechst AG) describe isoquinolines including 3-piperidino, 3-piperazino, and 3-piperazino N-substituted derivatives that are reported to exhibit antidepresssant activity.

U.S. Pat. No. 3,641,032 to Zinnes et al. (Warner Lambert Co.) describes immunosuppressive compositions that include 2-ethyl-3-hydroxy-1(2H)-isoquinolone dipenylcarbamate.

U.S. Pat. No. 3,870,721 to Archibald et al. relates to 4-alkanoylamino isoquinolinediones and 3-alkanoyloxy-4-alkanoylamino isoquinolones. A representative isoquinolinedione reported to inhibit platelet aggregation is 4-acetamido-1,2,3,4-tetrahydro 1,3-isoquinolinedione.

U.S. Pat. No. 3,954,771 to Geerts et al., assigned to UCB Society Anonyme, describes a process for the preparation of 2H-isoquinolin-3-ones. The foregoing compounds are described as precursors for synthesis of 1,4-dihydro-1,4-ethanoisoquinoline-3(2H)-ones (described in U.S. Pat. No. 3,781,436) that are reported to be active in the central nervous system for treatment of disorders including insomnia and vertigo.

U.S. Pat. No. 4,041,077 to Ghosez et al. (UCB Societe Anonyme) describes the use of N-benzyl-2,2-dimethoxyacetamides in the synthesis of 2H-isoquinolin-3-ones which, in turn, may be used in the synthesis of 1,4-dihydro-1,4-ethanoisoquinolin-3(2H)-ones.

DETAILED DESCRIPTION OF THE INVENTION

O-Functionalized-4-substituted isoquinolin-3-ol derivatives, pharmaceutical compositions containing an O-functionalized-4-substituted isoquinolin-3-ol derivative as an active ingredient, methods of treating a mammal exhibiting a cardiac condition and methods for synthesizing the present compounds are contemplated.

In particular, the invention contemplates an O-functionalized 4-substituted isoquinolin-3-ol having a structure that corresponds to the formula I:

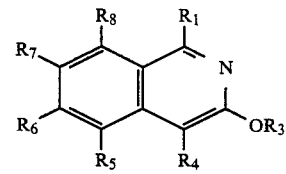

wherein $R_1$ is a radical selected from the group consisting of hydrogen, lower alkyl, aryl, and halogen-substituted radicals thereof;

$R_3$ is a radical selected from the group consisting of lower alkyl, acyloxyalkyl, amino lower alkyl, lower alkylamino lower alkyl, lower dialkylamino lower alkyl, cycloalkyl, aralkyl, aryl, alkenyl, alkynyl, or an acyl or sulfonyl radical of the formula $Y(O)_nR$ wherein Y is carbon or sulfur and n is an integer having a value of 1 when Y is carbon and having a value of 2 when Y is sulfur, and R is hydrogen (except when Y is sulfur), lower alkyl, amino lower alkyl, lower alkylamino lower alkyl, lower dialkylamino lower alkyl, cycloalkyl, aralkyl, aryl, lower alkenyl, lower alkynyl, an amino radical of formula NR′R″ wherein R′ and R″ are independently selected from hydrogen, lower alkyl, amino lower alkyl, lower alkylamino lower alkyl and lower dialkylamino lower alkyl, cycloalkyl, aralkyl, aryl, alkenyl or alkynyl, or R′ and R″ together with the nitrogen may form a heterocyclic or a substituted heterocyclic ring having 3–8 carbon atoms such as, for example, a morpholino, pyrrolidino, piperidino and an azepino ring, or a piperazino or a substituted piperazino ring wherein the substituted is lower alkyl, lower alkoxy carbonyl, phenyl or substitued phenyl wherein the substituent is lower alkoxy, lower alkyl, nitro or halo; or a radical of formula $OR'''$ wherein $R'''$ may be lower alkyl, amino lower alkyl, lower alkylamino lower alkyl and lower dialkylamino lower alkyl, cycloalkyl, aralkyl, aryl, alkenyl or alkynyl; and $R_4$ is a radical selected from the group consisting of lower alkyl and halogen-substituted lower alkyl, cycloalkyl, aralkyl, aryl and halogen-substituted aryl, lower alkenyl, lower alkynyl, halogen, cyano, nitro, nitroso, an amino radical of the formula $NR'R''$ wherein $R'$ and $R''$ are as defined above, $NR''COR'$ wherein $R'$ and $R''$ independently are as defined above, $N(COR')_2$ wherein $R'$ is as defined above, $COR'$ or $COOR'$ wherein $R'$ is as defined above, $CONR'R''$ wherein $R'$ and $R''$ independently are as defined above, $-(CH_2)_x-Z$ wherein x is an integer from 1 to about 8, inclusive, preferably from 1 to about 4, and Z is cyano, $OR'$, $OCOR'$, $COOR'$, or $CONR'R''$ wherein $R'$ and $R''$ independently are as defined above, radicals of the formula $N(CONHR')_2$ wherein $R'$ is as defined above, radicals of the formula $NHCO(Q)(R')_p$ wherein Q is oxygen or $N(H)_m$ and $R'$ is as defined above, with the proviso that when Q is oxygen, $R'$ is other than hydrogen and p is 1, and that when Q is $N(H)_m$, m and p independently may be zero, 1, or 2 provided that the sum of m and p is 2; and $R_5$, $R_6$, $R_7$, and $R_8$ may be independently selected from the group consisting of hydrogen, halogen, hydroxy, acyloxy, carbamyloxy, lower alkylcarbamyloxy and lower alkoxy; and $R_5$ and $R_6$, $R_6$ and $R_7$ or $R_7$ and $R_8$ when taken together may form a ring such as a methylenedioxy ring.

The preferred compounds of this invention include those compounds wherein $R_1$ is lower alkyl or halo lower alkyl; $R_3$ is lower alkyl, aralkyl, acyloxyalkyl or $Y(O)_nR$; $R_4$ is nitro, $N(COR')_2$, $N(CONHR')_2$, $COOR'$, $NR'R''$, $NR''COR'$ and $NHCO(Q)(R')_p$; $R_6$ and $R_7$ are lower alkoxy, carbamyloxy or hydrogen; and $R_5$ and $R_8$ are hydrogen.

Also contemplated are pharmaceutically acceptable salts of a compound of this invention. Any conventional pharmaceutically acceptable salt can be used. Among the salts that can be prepared are acid addition salts prepared from organic and inorganic acids such as, for example, hydrochloric acid, hydrobromic acid, phosphoric acid, hypophosphoric acid, methanesulfonic acid, p-toluenesulfonic acid and sulfuric acid.

Exemplary compounds of the present invention whose structures conform to the above formula are listed in Table 1, below.

As used herein the term "lower alkyl" indicates a branched or straight chain hydrocarbon having 1 to about 8 carbon atoms, and particularly 1 to about 4 carbon atoms. Lower alkyl radicals include, for example, methyl, ethyl, propyl, isopropyl, n-butyl, sec-butyl, t-butyl, n-pentyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1-octyl, 2-octyl, and the like. The term "cycloalkyl" indicates a cyclic alkyl group having 3 to about 7 carbon atoms. The term "lower alkenyl" indicates a branched or straight chain hydrocarbon having about 3–5 carbon atoms such as 2-butenyl, 3-butenyl, allyl and isopentenyl, for example. The term "lower alkynyl" indicates a branched or straight chain hydrocarbon having about 2–5 carbon atoms such as acetylenyl, 1-propynyl and 1-butynyl.

The term "aryl", as used herein alone or in combination with other terms, indicates aromatic hydrocarbon groups, such as phenyl or naphthyl groups, which can be unsubstituted or substituted with one or more groups selected from lower alkyl radicals, halo lower alkyl radicals, hydroxy, lower alkoxy, lower alkylthio, halogens, nitrile, nitro, amino, sulfonic acid derivatives, or carboxylic acid derivatives COX wherein X is hydroxy, lower alkoxy, or $NR'R''$ wherein $R'$ and $R''$ independently may be hydrogen or as defined above, for example.

The term "aralkyl" indicates a radical containing a lower alkyl group substitued with an aryl radical or substituted aryl radical as defined above.

The phrase "halogen-substitued radical" indicates a lower alkyl or aryl group (in the case of $R_1$) and a lower alkyl, aryl or lower alkoxy-substituted aryl (in the case of $R_4$) that includes a halogen selected from chloro, bromo, iodo and fluoro.

The term "lower alkoxy" indicates a radical containing a lower alkyl group (as defined above) and an oxygen atom at the terminus. Examples include methoxy, ethoxy, isopropoxy, n-butoxy and the like, with lower alkoxy having 1 to about 4 carbon atoms being particularly preferred.

A pharmaceutical composition that comprises an effective amount of an above-described isoquinoline derivative dispersed in a pharmaceutically acceptable carrier is also contemplated herein. The composition comprises a unit dosage of the isoquinoline derivative.

Isoquinoline derivatives of this invention have cardiotonic and/or renal vasodilating properties and/or inhibit the hydrolytic activity of phosphodiesterase fraction III. In preferred practice, the isoquinoline derivative of the pharmaceutical composition is capable of producing the desired cardiovascular effect in the amount at which that isoquinoline derivative is present in the pharmaceutical composition when that composition is introduced as a unit dose into an appropriate mammal.

The term "unit dosage" and its grammatical equivalents are used herein to refer to discrete units suitable for administration to human patients and to warm-blooded mammals. Each unit contains a predetermined effective amount of the active ingredient calculated to produce the desired cardiostimulating and/or vasodilating and/or phosphodiesterase inhibiting effect in association with the required physiologically tolerable carrier, e.g. a diluent or a vehicle.

The specifications for the novel unit dosage forms of this invention are dictated by and are directly dependent upon (a) the unique characteristics of the active ingredient and (b) the limitations inherent in the art of compounding such an active ingredient for therapeutic use in humans and other mammals. Examples of suitable unit dosage forms in accord with this invention are tablets, capsules, pills, powder packets, granules, wafers, and the like, segregated multiples of any of the foregoing, along with liquid solutions, liquid suspensions, elixirs and aerosol suspensions.

The active ingredient is referred to herein as being dispersed in the carrier. Thus the dispersion formed can be a simple admixture, a non-settling dispersion as in the case of certain emulsions or an ultimate dispersion, a true solution. In such compositions, the active ingredient is ordinarily present in an amount of at least about 0.5 percent by weight based on the total weight of the composition to about 90 percent by weight.

The effective amount of active ingredient that is administered in vivo depends on the age and weight of the mammal treated, the particular condition to be treated, the frequency of administration, and the route of administration. Exemplary unit doses can contain about 0.01 to about 100 milligrams per kilogram of body weight, more preferably about 0.1 to 20 milligrams per kilogram of body weight. The human adult dose is typically about 100 to about 500 milligrams daily, given as a single dose or in 3 or 4 divided doses. Veterinary dosages correspond to human dosages with the amounts administered being in proportion to the weight of the animal as compared to adult humans. It will be understood that the amount administered is determined by the physician or veterinarian in light of the relevant circumstances including the condition to be treated, the compound to be administered and the route of administration. Therefore, the foregoing dosage ranges are not intended to limit the scope of this invention in any way.

Pharmaceutically acceptable carriers are those well known in the art. The carrier may take a wide variety of forms depending on the form of preparation desired for administration, e.g., intravenous, oral or parenteral.

Liquid compositions include liquid phases in addition to or with the exclusion of water. Exemplary of such liquid phases are glycerin and vegetable oils including peanut oil and cottonseed oil.

Suitable solid carriers (diluents) include those materials usually used in the manufacture of pills, capsules or tablets, and include cornstarch, lactose, dicalcium phosphate, thickeners such as tragacanth and methylcellulose U.S.P., finely divided silica, polyvinylpyrrolidinone, magnesium stearate and the like. Antioxidants such as methylparaben and propylparaben can be present in both liquid and solid compositions, as can sweeteners such as cane sugar, beet sugar, sodium saccharin, sodium cyclamate and the dipeptide methyl ester sweetener sold under the trademark NUTRASWEET (aspartame) by G. D. Searle Co., Skokie, IL.

Methods for stimulating cardiac contractions, increasing contractile force of cardiac muscle and/or dilating renal vasculature in a mammal are also contemplated. The methods comprise administering to that mammal a unit dose of a pharmaceutical composition that includes an effective amount of an active ingredient that is an aforementioned isoquinoline derivative dispersed in a pharmaceutically acceptable carrier.

The pharmaceutical composition can be administered orally, by injection, by inhalation (for example, in the form of an aerosol, micropulverized powder or nebulized solution) or by any other means well known in the art.

Inasmuch as a pharmaceutical composition can be administered 2 or more times daily, the methods include the serial administration of the pharmaceutical composition into the treated mammal over a given time period.

Methods for synthesizing the particular O-functionalized 4-substituted isoquinolin-3-ol derivatives of this invention are other aspects of the present invention.

The following examples describe the invention in greater particularity and are intended to be a way of illustrating but not limiting the invention.

METHODS OF PREPARATION

The various 3-O-functionalized-4-substituted isoquinolin-3-ol derivatives of this invention can be prepared by one of the following general methods.

The starting materials for the various compounds of this invention are 4-substituted isoquinolin-3-ol compounds I wherein $R_3$ is H, and are prepared according to the processes described in our co-pending applications No. 871,967 filed on June 9, 1986 and No. 882,655 filed on July 7, 1986.

The various ether derivatives of this invention represented by formula I wherein $R_3$ is alkyl, aminoalkyl, cycloalkyl, aralkyl or acyloxymethyl are prepared by reacting the parent isoquinolin-3-ol compounds I, wherein $R_3$ is H, with an alkali metal derived base or preferably a silver metal derived base such as hydride, oxide, alkoxide, hydroxide, carbonate or an organic base such as a tertiary amine, for example triethylamine, pyridine, dialkylaniline etc., and with an organic compound such as $R_3X$ wherein X is a reactive species such as $OSO_2R_{10}$ or a halogen and $R_3$ is as already defined and $R_{10}$ is lower alkyl, phenyl or substituted phenyl wherein the substituent is lower alkyl, halo or nitro. The reaction may be carried out in an organic solvent such as an ether, chlorohydrocarbon, hydrocarbon or preferably in an aprotic polar solvent such as dimethylformamide, dimethylsulfoxide or hexamethylphosphoramide. In a variation of the above method it is also possible to first form the metal salt of compounds I wherein $R_3$ is a metal cation as already defined, by reacting 3-isoquinolinol I where $R_3$ is H with the desired metal-derived base and then reacting this salt with a reactive organic compound $R_3X$ as already defined.

The various 3-acyloxy and 3-sulfonyloxy derivatives I wherein $R_1, R_4-R_8$ are as already defined and $R_3$ is $Y(O)_nR$ wherein Y is carbon or sulfur, and n is an integer of value 1 when Y is carbon and 2 when Y is sulfur, and R is as already defined, are prepared by treating the isoquinolin-3-ol I wherein $R_3$ is H with the various acyl anhydrides $O[Y(O)_nR]_2$ or acyl halides $XY(O)_nR$ wherein X is a halogen, and Y, R and n are as previously defined, either neat or in an organic solvent such as benzene, toluene etc., a chlorohydrocarbon or an ether such as diethyl ether, tetrahydrofuran or dioxane, at temperatures ranging from $-5°$ C. to reflux temperatures. Alternatively the acylation of isoquinolin-3-ols with an acyl halide or anhydride may be carried out using a metal derived base such as a metal hydride, hydroxide, carbonate etc. or an organic base such as triethylamine, pyridine, dialkylaniline and the like. A catalyst such as 4-dialkylamino pyridine may also be added in these cases.

Acylation of I wherein $R_3$ is H and $R_4$ is amino or acylamino with an excess of anhydride or acyl halide by either of the above two methods (i.e. heating with an acylating agent or treating with an acylating agent in presence of a base) gives triacyl derivative I wherein $R_3$ is acyl and $R_4$ is diacylamino.

The 4-nitro or 4-nitroso derivatives I ($R_4$ is $NO_2$ or NO and $R_3$ is other than H, as defined above) can be reduced, for example by hydrogenation, to obtain 4-amino derivatives I wherein $R_4$ is $NH_2$.

The 4-amino derivative I (wherein $R_4$ is amino and $R_3$ is other than H, as already defined) can be treated with an acid chloride or an anhydride to provide a 4-acylamino derivative I (wherein $R_4$ is NHCOR″ with R″ as described above); with an inorganic cyanate (for example NaOCN) in an acidic medium (such as acetic acid) to provide the corresponding urea I (wherein $R_4$ is NHCONH$_2$ and $R_3$ is other than H as already defined); with an organic isocyanate to provide a substituted urea I wherein $R_4$ is NHCONHR' and R' is as described above but other than H and $R_3$ is other than H as already defined; and/or a biuret derivative I wherein $R_4$ is N(CONHR')$_2$ wherein R' is as defined above and $R_3$ is other than H as described above; with an N,N-disubstituted carbamoyl chloride to provide an N,N-disubstituted urea I wherein $R_4$ is NHCONR'$_2$ with R' as defined above and $R_3$ other than H as defined above; or with a chloroformate to provide a carbamate I wherein $R_4$ is NHCOOR' and R' is as defined above.

I wherein $R_4$ is as already defined and $R_3$ is a 4-protected piperazinecarbonyl moiety such as —CON[(CH$_2$)$_2$]$_2$NCOOR$_9$ and $R_9$ is an alkyl moiety, for example t-butyl, can be converted into the corresponding unmasked piperazine derivative —CON[(CH$_2$)$_2$]$_2$NH by treatment with a strong acid such as trifluoroacetic acid.

Treatment of I wherein $R_1$ is CH$_3$, $R_3$ is other than H as already defined and $R_4$ is as already defined, with a halogen or preferably with a halogenating reagent such as for example, N-halosuccinimide, gives the corresponding 1-halomethyl derivatives I wherein $R_1$ is CH$_2$X and X is a halogen such as chlorine, bromine or iodine.

A list of compounds that correspond to the foregoing formula, their biological activities and experimental procedures for their preparation are included in the following discussion.

A series of O-functionalized isoquinolin-3-ol derivatives that were synthesized according to the various methods of the present invention are listed in Table 1.

Having generally described the invention, a more complete understanding can be obtained by reference to the following Examples, which are included for illustrative purposes only and are not intended to be limiting.

BEST MODES OF CARRYING OUT THE INVENTION

In the following Examples, melting points (mp) were determined on a Thomas-Hoover apparatus, and the melting points reported herein are uncorrected. The infrared (IR) spectra were recorded on a Beckman Instruments IR-8 spectrophotometer and are expressed in cm$^{-1}$. Nuclear magnetic resonance (NMR) spectra for hydrogen atoms were obtained in the indicated solvent with tetramethylsilane (TMS) as the internal standard on a Varian T-60A or an IBM WP-100 spectrometer. The values are expressed in delta ($\delta$) units downfield from TMS. Parenthesized, underlined hydrogens were assigned to the resonance positions immediately before the parenthesis. Mass spectra were obtained on a Finnigan 1015D quadrupole mass spectrometer coupled to a Finnigan 9500 gas chromatograph or on a Finnigan MAT 8230 Double Focusing high resolution mass spectrometer.

EXAMPLE 1

4-Carbomethoxy-3-ethoxy-6,7-dimethoxy-1-methylisoquinoline (19)

A slurry of 4-carbomethoxy-3-hydroxy-6,7-dimethoxy-1-methylisoquinoline (0.500 g, 1.81 mmol) and silver carbonate (0.498 g, 1.81 mmol) in dimethylformamide (15 mL) was stirred for 20 minutes and then iodoethane (0.326 g, 2.09 mmol) was added and the slurry was stirred at room temperature for two days. The silver iodide precipitate was filtered off and the filtrate was diluted with water (75 mL) and extracted with ether (3×40 mL). The ether was successively washed with water and saturated sodium chloride solution and dried (Na$_2$SO$_4$). The ether was evaporated in vacuo and the solid residue was triturated with ether/hexane to give the title compound (310 mg, 56% as a pale yellow solid, mp 147°–149° C. IR (KBr): 1709, 1629, 1572 cm$^{-1}$. NMR (CDCl$_3$): $\delta$ 1.40 (t, 3H, 4-OCH$_2$CH$_3$), 2.80 (s, 3H, 1-CH$_3$), 3.98 (s, 9H, 6,7-ArOCH$_3$ and 4-COOCH$_3$); 4.50 (q, 2H, 4-OCH$_2$CH$_3$); MS: 305 (M+).

Anal. Calcd. for C$_{16}$H$_{19}$NO$_5$·¼H$_2$O: C, 62.02; H, 6.34; N, 4.52; Found: C, 61.89; H, 6.34; N, 4.45

EXAMPLE 2

3-Acetoxy-6,7-dimethoxy-1-methyl-4-nitroisoquinoline (2).

A slurry of 3-hydroxy-6,7-dimethoxy-1-methyl-4-nitroisoquinoline (0.528 g, 2 mmol) in acetic anhydride (5 mL) was stirred and heated with an oil bath to gentle reflux (ca. 150° C.). The slurry became a clear dark solution within 10 minutes. After 1 hour the reaction mixture was cooled and the excess acetic anhydride was removed under vacuum. The solid residue was triturated with ether and dried to give a tan solid (0.566 g, 92.5%), mp >300° C. IR (KBr): 1786, 1621, 1600, 1565, 1513, 1435, 1264, 1170 cm$^{-1}$; NMR (CDCl$_3$): $\delta$ 2.35 s, 3H, 3-OCOCH$_3$), 4.05 (s, 6H, OCH$_3$), 7.28 (s, 1H, ArH), 7.32 (s, 1H, ArH); MS: 306 (M+), 264 (M+—O=C=CH$_2$).

Anal. Calcd. for C$_{14}$H$_{14}$N$_2$O$_6$: C, 54.90; H, 4.61; N, 9.15 Found: C, 54.73; H, 4.65; N, 9.16

EXAMPLE 3

3-Diethylcarbamyloxy-6,7-dimethoxy-1-methyl-4-nitroisoquinoline (27)

To a slurry of 3-hydroxy-6,7-dimethoxy-1-methyl-4-nitroisoquinoline (1.90 g, 7.19 mmol) in methylene chloride (100 mL) were added triethylamine (1.5 mL, 10.78 mmol), 4-dimethylaminopyridine (176 mg, 1.44 mmol) followed by diethylcarbamoyl chloride (0.81 mL, 8.62 mmol) in 5 mL of methylene chloride), added over a 10 minute period. The addition of each of the last three reagents was repeated twice two hours apart and then the mixture was stirred at room temperature overnight. The clear dark red-brown solution was washed with water (3×150 mL), saturated sodium bicarbonate solution and again with water. The organic phase was dried (Na$_2$SO$_4$), filtered and evaporated to dryness in vacuo. The tan residue was recrystallized from methylene chloride/ether to yield the title compound (2.04 g, 92.1%), mp 220°–221° C. (d). IR (KBr): 1738, 1520, 1260 cm$^{-1}$. NMR (CDCl$_3$): $\delta$ 1.24 and 1.28 [two t, J=7 Hz, total 6H, N(CH$_2$CH$_3$)$_2$], 2.90 (s, 3H, 1-CH$_3$), 3.20–3.80 (m, 4H, N(CH$_2$CH$_3$)$_2$), 4.03 (s, 6H, 5,6-OCH$_3$), 7.24 (s, 1H, 5- or 8-H), 7.28 (s, 1H, 5- or 8-H); MS (DCI): 364 (MH)+

Anal. Calcd. for C$_{17}$H$_{21}$N$_3$O$_6$: C, 56.19; H, 5.83; N, 11.56 Found: C, 56.07; H, 6.25; N, 11.53

EXAMPLE 4

4-Amino-3-(diethylcarbamyloxy)-6,7-dimethoxy-1-methylisoquinoline (31)

A slurry of 3-(diethylcarbamyloxy)-6,7-dimethoxy-1-methyl-4-nitroisoquinoline (500 mg, 1.38 mmol) in methanol (50 mL) was hydrogenated in a Parr hydrogenator over 10% Pd/C (100 mg) for 4 hours. The reaction mixture was filtered through a celite pad, the solids were washed with methanol and the combined filtrate and washings were evaporated to dryness in vacuo to yield a yellow solid residue. One recrystallization from methylene chloride/ether afforded pure title compound (437 mg, 95.3%), mp 206°–207° C. IR (KBr) 3455, 3340, 3220, 1720, 1655, 1495, 1440, 1265, 1160 cm$^{-1}$; NMR (CDCl$_3$): δ 1.25 and 1.30 (two partly superimposed br t, 6H, N(CH$_2$CH$_3$)$_2$], 2.67 (s, 3H, 1-CH$_3$), 3.20–3.70 [br m, 4H, N(CH$_2$CH$_3$)$_2$], 3.93 (s, 3H, OCH$_3$), 3.98 (s, 3H, OCH$_3$), 6.82 (s, 1H, 5- or 8-H), 6.93 (s, 1H, 5- or 8-H); MS (DCI): 334 (MH)+

Anal. Calcd. for C$_{17}$H$_{23}$N$_3$O$_4$.½H$_2$O: C, 59.63; H, 7.02; N, 12.27; Found: C, 59.76; H, 7.22; N, 11.92

EXAMPLE 5

3-Diethylcarbamyloxy-6,7-dimethoxy-1-methyl-4-ureidoisoquinoline (47)

To a solution of 4-amino-3-(diethylcarbamyloxy)-6,7-dimethoxy-1-methylisoquinoline (1.0 g, 3 mmol) in acetic acid (10 mL) was added sodium cyanate (0.23 g, 3.6 mmol) and the mixture was stirred under nitrogen at room temperature for 72 hours. Then the mixture was evaporated to dryness in vacuo and the residue triturated with water to give a gelatinous precipitate which was collected (0.69 g). The filtrate gave additional solids (0.50 g). The combined solids were dissolved in chloroform and purified by low pressure column chromatography on a silica gel column. Elution with 1.8% methanol/chloroform gave purified title compound which was collected from methylene chloride/ether as a colorless crystalline solid (0.865 g, 68.7%), mp 215°–216° C. IR (KBr): 3323, 3316, 3313, 3199, 1712, 1697, 1667, 1428 cm$^{-1}$; NMR (CDCl$_3$): δ 1.23 and 1.28 [each t, J=7 Hz, total 6H, N(CH$_2$CH$_3$)$_2$], 2.80 (s, 3H, 1-CH$_3$), 3.20–3.70 [br m, 4H, N(CH$_2$CH$_3$)$_2$], 4.98 (s, 2H, NHCONH$_2$), 6.78 and 7.01 (two s, each 1H, 5,8-H), 6.876 (br s, 1H, 4-NH). MS (DCI): 377 (MH)+; UV (EtOH) nm: 247 (ε51600), 275 (ε4800), 287 (ε5050), 297 (ε5000).

Anal. Calcd. for C$_{18}$H$_{24}$N$_4$O$_5$: C, 57.44; H, 6.43; N, 14.88; Found: C, 57.36; H, 6.81; N, 14.71

EXAMPLE 6a 1,5-Dibutyl-3-[3-(diethylcarbamyloxy)-6,7-dimethoxy-1-methylisoquinolin-4-yl]biuret (37).

To a solution of 4-amino-3-(diethylcarbamyloxy)-6,7-dimethoxy-1-methylisoquinoline (410.5 mg, 1.24 mmol) in methylene chloride (20 mL) was added n-butylisocyanate (2, 0.17 mL, 1.49 mmol, 1.2 eq.) and the solution was stirred at room temperature overnight. TLC analysis (40% ethyl acetate/chloroform) revealed the presence of a small amount of unreacted starting material. Therefore, additional isocyanate (0.17 mL, 1.49 mmol, 1.2 eq; total 0.34 mL, 2.98 mmol, 2.4 eq) was added and the mixture was stirred at room temperature overnight. Then the mixture was heated to reflux for an additional 48 hours. The crude mixture was separated on a low pressure silica gel column using ether/petroleum ether. Two products were isolated. The slower moving product is described in Example 6b. The faster moving product weighed 205 mg (31%) and had mp 138°–140° C. IR (KBr): 3360, 1700, 1650, 1610, 1500, 1420, 1142 cm$^{-1}$; NMR (CDCl$_3$): δ 0.85 (br t, J=7 Hz, 6H, N(CH$_2$-CH$_3$)$_2$], 1.10–1.70 [br m, 14H, N(CH$_2$CH$_3$)$_2$ +H$_2$C(CH$_2$)$_2$-CH$_3$], 2.88 (s, 3H, 1-CH$_3$), 3.0–3.70 [m, 8H, CON(CH$_2$CH$_3$)$_2$+N[CH$_2$(CH$_2$)$_2$CH$_3$]$_2$, 3.95 (s, 3H, OCl$_4$)$_3$ OCH$_3$ 4.02 (s, 3H, OCH$_3$), 6.88 (s, 1H, 5- or 8-H), 7.27 (s, 1H, 5- or 8-H), 7.35 (m, 1H, CONH); MS (FAB): 532 (MH)+; UV (EtOH) nm: 241 (ε59060), 273 (ε4740), 286 (ε4700), 298 (ε4755), 322 (ε4390), 344 (ε4700).

Anal. Calcd. for C$_{27}$H$_{41}$N$_5$O$_6$: C, 61.00; H, 7.98; N, 13.17; Found: C, 61.39; H, 7.77; N, 12.70

EXAMPLE 6b

4-[N'-(n-Butylureido)]-3-diethylcarbamyloxy-6,7-dimethoxy-1-methylisoquinoline (38).

From the mixture of the products obtained in Example 6a, the major and the slower moving product isolated by column chromatography was recrystallized from ether/petroleum ether to give purified title compound (0.34 g, 63.5%), mp 201°–202° C. IR (KBr): 3360, 3220, 1715, 1635, 1230, 1150 cm$^{-1}$; NMR (CDCl$_3$): δ 0.83 [br t, J=7 Hz, 6H, N(CH$_2$CH$_3$)], 1.00–1.50 [m, 10H, (CH$_2$)$_2$CH$_3$, N(CH$_2$CH$_3$)], 2.83 (s, 3H, 1-CH$_3$), 3.00–3.70 (m, 6H, NCH$_2$), 3.90 (s, 3H, OCH$_3$), 4.01 (s, 3H, OCH$_3$), 4.97 (m, 1H, NHCONH-CH$_2$, D$_2$O exchanged), 6.16 (s, 1H, 4-NHCO, D$_2$O exchanged), 7.00 (s, 1H, 5- or 8-H), 7.10 (s, 1H, 5- or 8-H); MS (FAB): 433 (MH)+.

Anal. Calcd. for C$_{22}$H$_{32}$N$_4$O$_5$: C, 61.09; H, 7.46; N, 12.95; Found: C, 61.32; H, 7.65; N, 12.60

EXAMPLE 7a

3-Acetoxy-4-(N,N-diethylamino)-6,7-dimethoxy-1-methylisoquinoline ¼ Hydrate (29).

3-Hydroxy-6,7-dimethoxy-1-methyl-4-nitroisoquinoline (1.0 g, 3.78 mmol) was slurried in acetic anhydride (60 mL) and hydrogenated over 10% Pd/C in a Parr hydrogenator under 25 psi hydrogen at room temperature for 15 hour. The reaction mixture was filtered through celite and the solids were washed with chloroform. The combined yellow filtrate and washings were evaporated to dryness in vacuo to give a solid residue. Upon trituration of this solid residue with ether was obtained a light yellow solid (0.42 g, 3-O, 4-N,N-triacetyl derivative of the corresponding 4-amino-3-isoquinolinol). Concentration of the filtrate from the trituration yielded the title compound as a colorless crystalline solid (340 mg, 26%), mp 141°–142° C. IR (KBr) 1765, 1210 cm$^{-1}$; NMR (CDCl$_3$): δ 1.00 [t, J=7 Hz, 6H, N(CH$_2$CH$_3$)], 2.37 (s, 3H, OCOCH$_3$), 2.82 (s, 3H, 1-CH$_3$), 3.11 [q, J=7 Hz, 4H, N(CH$_2$CH$_3$)], 4.03 [s, 6H, 6,7-(OCH$_3$)$_2$], 7.18 (s, 1H, 5- or 8-H); 7.77 (s, 1H, 5- or 8-H); UV (EtOH) nm: 245 (ε40500), 320 (ε4090), 332 (68 4110); MS (DCI): 333 (MH)+.

Anal. Calcd. for C$_{18}$H$_{24}$N$_2$O$_4$.¼H$_2$O: C, 64.17; H, 7.33; N, 8.32; Found: C, 64.52; H, 7.45; N, 8.39

EXAMPLE 7b 6,7-Dimethoxy-1-methyl-4-[N-propanamido]-3-propanoyloxyisoquinoline (33)

A slurry of 3-hydroxy-6,7-dimethoxy-1-methyl-4-nitroisoquinoline (1.0 g, 3.78 mmol) in propionic anhydride (100 mL) was hydrogenated over 10% Pd/C at 38 psi for 24 h. The reaction mixture was filtered through a celite pad and the solids were washed with chloroform. The combined filtrate and washings were evaporated to dryness in vacuo to yield a solid residue. The solid was triturated with ether, filtered and again washed with ether to yield the title compound as a light yellow solid (0.73 g, 68%), mp 250°–253° C. IR (KBr): 3225, 3180, 1770, 1655, 1490, 1260 cm$^{-1}$; NMR (CDCl$_3$): δ 1.28 (t, J=7 Hz, 6H, COCH$_2$CH$_3$), 2.67 (q, J=7 Hz, 4H, COCH$_2$CH$_3$), 2.80 (s, 3H, 1-CH$_3$), 3.93 (s, 3H, OCH$_3$), 4.02 (s, 3H, OCH$_3$), 6.80–7.30 (br m, 3H, 5,8-H, NH); UV (EtOH) nm: 247 (ε46600), 288 (ε4590), 320 (ε3760), 333 (ε3480); MS (DCI): 347 (MH)$^+$.

Anal. Calcd. for C$_{18}$H$_{22}$N$_2$O$_5$: C, 62.42; H, 6.40; N, 8.00; Found: C, 62.21; H, 6.47; N, 8.14

EXAMPLE 8

4-N,N-Diacetamido-3-acetoxy-6,7-dimethoxy-1-methylisoquinoline (17).

A slurry of 4-acetamido-3-hydroxy-6,7-dimethoxy-1-methylisoquinoline (0.63 g, 2.28 mmol) in acetic anhyride (5 mL) was heated under reflux for 15 minutes to form a clear solution. After cooling to room temperature the excess acetic anhydride was removed in vacuo and the colorless solid residue was triturated with methanol (2 mL) and ether (40 mL) for 1 hour. The crystalline colorless solid that separated was isolated by filtration, washed with ether and dried in vacuo to provide the title compound (0.62 g, 85.6%), mp 200°–201° C. IR (KBr): 1760, 1730, 1700, 1620, 1560, 1510, 1485, 1325, 1200 cm$^{-1}$; NMR (CDCl$_3$): δ 2.32 (s, 9H, COCH$_3$), 2.88 (s, 3H 1-(CH$_3$), 3.98 (s, 3H, ArOCH$_3$), 4.02 (s, 3H, ArOCH$_3$), 6.78 (s, 1H, 5- or 6-H), 7.28 (s, 1H, 5- or 6-H); MS: 360 (M$^+$), 318 (M$^+$-COCH$_3$), 276 (218-CH$_2$=C=O); MS (FAB): 361 (M+1)$^+$ Anal. Calcd. for C$_{18}$H$_{20}$N$_2$O$_6$ (360.4): C, 59.99; H, 5.59; N, 7.77; Found: C, 59.78; H, 5.47; N, 7.73

EXAMPLE 9

6,7-Dimethoxy-1-methyl-4-nitro-3-(1-piperazinyl)carbonyloxyisoquinoline (70)

3-(4-t-Butoxycarbonylpiperazin-1-yl)carbonyloxy-6,7-dimethoxy-1-methyl-4-nitroisoquinoline (20 g, 4.20 mmol) was added in small portions over 20 minutes to trifluoroacetic acid (15 mL), stirred and cooled to −10° C. (ice-methanol bath). The mixture was stirred at −10° C. for an additional 30 minutes and was then diluted with ice-water (100 mL). The solution was basified by adding 2N NaOH (150 mL) and then extracted with methylene chloride (3×100 mL). The combined organic extracts were dried (Na$_2$SO$_4$), filtered and evaporated to dryness in vacuo to yield a yellow solid residue. The solid was triturated thoroughly with ether, and was the collected and dried to yield the title compound as a yellow solid (1.49 g, 94.4%), mp |300° C. (d). IR (KBr): 3356, 1731, 1620, 1569, 1515, 1213 cm$^{-1}$; NMR (CDCl$_3$): δ 1.67 (br, s, 1H, NH); 2.90 (s, 3H, 1-CH$_3$), superimposed over 2.97 [br m, HN[(CH$_2$)]$_2$, 3.58 [br, s CON[(CH$_2$)]$_2$, 4.02 (s, 6H, 2×OCH$_3$), 7.25 (s, 1H, 5- or 8-H), 7.30 (s, 1H, 5- or 8-H); MS (DCI): 377 (MH)$^+$.

Anal. Calcd. for C$_{17}$H$_{20}$N$_4$O$_6$: C, 54.24; H, 5.37; N, 14.88; Found: C, 53.96; H, 5.36; N, 14.90

EXAMPLE 10

3-Acetoxy-1-bromomethyl-6,7-dimethoxy-4-nitroisoquinoline Hemihydrate (48).

A mixture of 3-acetoxy-6,7-dimethoxy-1-methyl-4-nitroisoquinoline (4.0 g, 13.06 mmol) in methylene chloride (100 mL) and N-bromosuccinimide (2.8 g, 15.66 mmol) was heated to reflux under nitrogen for 17 hours. The mixture was evaporated to dryness. The residue was redissolved in methylene chloride (60 mL) and the major product was isolated by chromatography on a silica gel column (low pressure) using 7:3 methylene chloride/hexane as the eluent to yield the title compound (2.13 g, 39%). One recrystallization from methylene chloride/ether gave the purified title compound as a lemon yellow crystalline solid (2.08 g, 38.7%), mp 194°–195° C. (d). IR (KBr) 1777, 1174 cm$^{-1}$; NMR (CDCl$_3$): δ 2.40 (s, 3H, OCOCH$_3$), 4.05 (s, 3H, OCH$_3$), 4.10 (s, 3H, OCH$_3$), 4.90 (s, 2H, 1-CH$_2$Br), 7.30 (s, 1H, B 5- or 8-H), 7.43 (s, 1H, 5- or 8-H); MS (DCI): 385 (MH)$^+$.

Anal. Calcd. for C$_{14}$H$_{13}$BrN$_2$O$_6$·½H$_2$O: C, 42.66; H, 3.58; N, 7.11; Found: C, 42.67; H, 3.49; N, 7.03

RESULTS

A. Cardiotonic Activity

The acute in vivo cardiotonic activity of compounds prepared according to the present invention was determined according to a modification of the procedure described by Alousi et al., Circ. Res., 45, 666 (1979).

In particular, adult mongrel dogs were anesthetized with sodium pentobarbital and were artificially respired. Arterial pressure was monitored via a femoral artery, and the pulse pressure was used to trigger a cardiotachometer for heart rate. Left ventricular pressure was determined with a Millar catheter, and dP/dT (the change in ventricular pressure with time) was derived. Cardiac output was determined by measuring ascending aortic blood flow with an electromagnetic flow probe, and myocardial contractile force was measured with a Walton Brodie strain gauge sutured to the right ventricle. Lead II EKG was also recorded.

A standard dose (10 µg/kg/min) of dopamine was administered to assess myocardial responsiveness.

Compounds of the invention were administered by intravenous infusion and the effects on cardiovascular parameters were determined. The total amount of each compound that was administered is shown in Table 3.

Dose related effects of the test compound on heart rate (HR), maximum change in left ventricular pressure with time (dP/dT), percent change in cardiac force (CF) and the change in mean arterial blood pressure (MABP) were compared to pretreatment control values and expressed as a percent change. Data for compounds of this invention are summarized in Table 3.

B. Renal Vasodilating Activity

Goldberg et al., J. Pharmacol. Exp. Ther., 163, 188 (1968), performed an investigation of the structural requirements for dopamine-like renal vasodilation of phenethylamines and apomorphine. The following procedure is a variation of the assay described in that report.

Adult mongrel dogs were anesthetized and surgically prepared for electromagnetic measurement of renal artery blood flow. A carotid artery was cannulated for measuring arterial blood pressure and drugs were administered intravenously or intraarterially (via the renal artery). Heart rate was monitored with a cardiotachometer. Renal vascular resistance was calculated as the ratio of mean arterial blood pressure to renal artery blood flow. Dopamine was infused intravenously at 3 µg/kg/min for ten minutes (at an infusion rate of about 1 ml/min) to determine responsiveness of each dog to renal dopamine receptor stimulation. Cumulative dose-response data were obtained by infusing a compound of this invention at progressively increasing (usually threefold) infusion rates, each dose being infused for five minutes. The maximum percent change from pre-drug control in renal artery blood flow (or in renal vascular resistance) was determined for each infusion dose.

Representative data for the isoquinoline derivatives of this invention are summarized in Table 2. RBF, RVR, MABP, and HR values are percent changes in renal blood flow, renal vascular resistance, mean arterial blood pressure, and heart rate, respectively, relative to control values.

C. Inhibition of Phosphodiesterase Fraction III Activity

Thompson et al. described a cyclic nucleotide phosphodiesterase assay in *Advances in Cyclic Nucleotide Research*, Brooker et al., eds., 10, 69–92 (1979). The following procedure is based on that published assay and measures the ability of compounds to inhibit cyclic nucleotide phosphodiesterase which is an enzyme that converts either cyclic AMP or cyclic GMP to the non-cyclized AMP or GMP, respectively.

Compounds were tested at various concentrations in the presence of cyclic AMP (0.10–1.0 µM containing 0.2 microCuries $^3$H-cyclic AMP), cyclic nucleotide phosphodiesterase, and 0.05M Tris-Cl buffer (pH 7.4, containing 5 mM magnesium chloride). After a specified time, the reaction was stopped by heating to 100° C. for 1 minute. After cooling, 0.10 ml of a solution containing snake venom (1 mg/ml) was added, and the reaction was allowed to proceed for 30 min. Termination of this reaction was accomplished by the addition of 1.0 ml of 33 percent DOWEX AG1×8 resin slurry (Dow Chemical Co., Midland, MI) to separate the product from the unconverted substrate. An aliquot was removed from the supernatant and analyzed by liquid scintillation spectrometry.

The fraction III enzyme was isolated as an isomzyme from the crude canine heart homogenate by ion exchange chromatography. The enzyme activity was designated fraction III since it is the third and last phosphodiesterase activity to be eluted from the chromatographic column. The fraction III enzyme has a relatively high affinity and specificity for the cyclic AMP.

Data are presented as the $IC_{50}$ which is the concentration (in micromoles) of a compound that was required to inhibit 50 percent of the cyclic nucleotide phosphodiesterase activity.

Data for the isoquinolinols of this invention are summarized in Table 4.

TABLE 1

O-Functionalized Isoquinolin-3-ol Derivatives

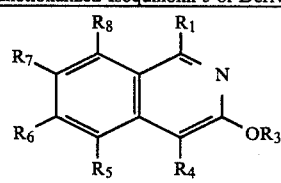

| Cmpd. | Ex. | R1 | R3 | R4 | R6 | R7 | MP. deg. C. |
|---|---|---|---|---|---|---|---|
| 1 | 2 | Me | Ac | Br | OMe | OMe | 194–196 |
| 2 | 2,3 | Me | Ac | NO$_2$ | OMe | OMe | >300 |
| 3 | 2 | Me | Ac | NO$_2$ | OMe | OEt | 230 (d) |
| 4 | 2 | Me | COEt | NO$_2$ | OMe | OEt | 173–175 |
| 5 | 3 | Me | COiPr | NO$_2$ | OMe | OEt | 177–178 |
| 6 | 3 | Me | SO$_2$Me | NO$_2$ | OMe | OEt | 209–210 (d) |
| 7 | 3 | Me | COPh | NO$_2$ | OMe | OMe | 207–210 (d) |
| 8 | 3 | Me | COPh | NO$_2$ | OMe | OEt | 207–209 (d) |
| 9 | 3 | Me | COtBu | NO$_2$ | OMe | OEt | 208–209 (d) |
| 10 | 3 | Me | CON(Me)$_2$ | NO$_2$ | OMe | OEt | 209–210 (d) |
| 11 | 3 | Me | CO—Ph—4-OMe | NO$_2$ | OMe | OEt | 204–206 (d) |
| 12 | 3 | Me | COtBu | NO$_2$ | OMe | OMe | 220 (d) |
| 13 | 3 | Me | CON(Me)$_2$ | NO$_2$ | OMe | OMe | 247–249 (d) |
| 14 | 3 | Me | CO—Ph—4-OMe | NO$_2$ | OMe | OMe | 209–210 (d) |
| 15 | 3 | Me | CO—Ph—4-Cl | NO$_2$ | OMe | OMe | 213–214 (d) |
| 16 | 3 | Me | SO$_2$Me | NO$_2$ | OMe | OMe | 205–206 (d) |
| 17 | 8 | Me | Ac | N(Ac)$_2$ | OMe | OMe | 200–201 |
| 18 | 1 | Me | iPr | COOMe | OMe | OMe | 137–138 |
| 19 | 1 | Me | Et | COOMe | OMe | OMe | 147–149 |
| 20 | 1 | Me | CH$_2$Ph | COOMe | OMe | OMe | 124–125 |
| 21 | 2 | Me | Ac | NO$_2$ | OEt | OMe | 210 (d) |
| 22 | 2 | Me | Ac | NO$_2$ | OMe | OnBu | 151–152 |
| 23 | 3 | Me | COtBu | NO$_2$ | OEt | OMe | 172–173 |
| 24 | 2 | Me | CON(Me)$_2$ | NO$_2$ | OEt | OMe | 211–212 |
| 25 | 2 | Me | SO$_2$N(Me)$_2$ | NO$_2$ | OMe | OMe | 198–199 |
| 26 | 2 | Me | SO$_2$N(Me)$_2$ | NO$_2$ | OMe | OEt | 203–204 (d) |
| 27 | 2 | Me | CON(Et)$_2$ | NO$_2$ | OMe | OMe | 220–221 (d) |
| 28 | 2 | Me | CON(Et)$_2$ | NO$_2$ | OMe | OEt | 207–208 (d) |
| 29 | 7a | Me | Ac | NEt$_2$ | OMe | OMe | 141–142 |
| 30 | 7a | Me | Ac | NEt$_2$ | OMe | OEt | 86–88 |
| 31 | 4 | Me | CON(Et)$_2$ | NH$_2$ | OMe | OMe | 206–207 |
| 32 | 2 | Me | Ac | NHCONH—Ph—4-OMe | OMe | OMe | 250–260 (d) |
| 33 | 7b | Me | COEt | NHCOEt | OMe | OMe | 250–253 (d) |
| 34 | 2 | Me | CON(Ph)$_2$ | NO$_2$ | OMe | OMe | 190–191 (d) |

TABLE 1-continued
O-Functionalized Isoquinolin-3-ol Derivatives

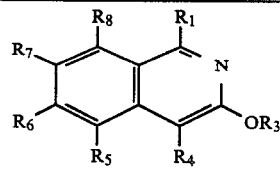

| Cmpd. | Ex. | R1 | R3 | R4 | R6 | R7 | MP. deg. C. |
|---|---|---|---|---|---|---|---|
| 35 | 2 | Me | CON(iPr)$_2$ | NO$_2$ | OMe | OMe | 229–230 (d) |
| 36 | 4 | Me | CON(Ph)$_2$ | NH$_2$ | OMe | OMe | 196–197 (d) |
| 37 | 6b | Me | CON(Et)$_2$ | N(CONH—nBu)$_2$ | OMe | OMe | 138–140 (d) |
| 38 | 6a | Me | CON(Et)$_2$ | NHCONH—nBu | OMe | OMe | 201–202 (d) |
| 39 | 4 | Me | CON(Me)$_2$ | NH$_2$ | OMe | OMe | 214–215 (d) |
| 40 | 6a | Me | CON(Me)$_2$ | NHCONH—allyl | OMe | OMe | 199.5–20 (d) |
| 41 | 2 | Me | COnPr | NO$_2$ | OMe | OMe | 138–139 |
| 42 | 2 | Me | COnBu | NO$_2$ | OMe | OMe | 131–132 |
| 43 | 4 | Me | SO$_2$N(Me)$_2$ | NH$_2$ | OMe | OMe | 185–187 (d) |
| 44 | 4 | Me | CON(Et)$_2$ | NH$_2$ | OMe | OEt | 161–162 (d) |
| 45 | 6a | Me | CON(Et)$_2$ | NHCONH—nBu | OMe | OEt | 190–191 |
| 46 | 6a | Me | CON(Et)$_2$ | NHCONH—Ph-4-CF$_3$ | OMe | OMe | 231–232 |
| 47 | 5 | Me | CON(Et)$_2$ | NHCONH$_2$ | OMe | OMe | 215–216 |
| 48 | 10 | CH$_2$Br | Ac | NO$_2$ | OMe | OMe | 194–195 (d) |
| 49 | 6b | Me | CON(Et)$_2$ | N(CONH—allyl)$_2$ | OMe | OMe | 135–136 |
| 50 | 6a | Me | CON(Et)$_2$ | NHCONH—allyl | OMe | OMe | 193–194 |
| 51 | 6a | Me | CON(Et)$_2$ | NHCONH—Ph-4-OMe | OMe | OMe | 215–217 |
| 52 | 2 | Me | CO—c-N(CH$_2$)$_4$ | NO$_2$ | OMe | OMe | 240 (d) |
| 53 | 4 | Me | CO—c-N(CH$_2$)$_4$ | NH$_2$ | OMe | OMe | 211–212 (d) |
| 54 | 6b | Me | CO—c-N(CH$_2$)$_4$ | N(CONH—nBu)$_2$ | OMe | OMe | 143 |
| 55 | 6a | Me | CO—c-N(CH$_2$)$_4$ | NHCONH—nBu | OMe | OMe | 205–206 |
| 56 | 6a | Me | CON(Et)$_2$ | NHCONH—Ph-4-CO$_2$Me | OMe | OMe | 218–219 |
| 57 | 6a | Me | CON(Ph)$_2$ | NHCONH—nBu | OMe | OMe | 241–242 |
| 58 | 4 | Me | CON(iPr)$_2$ | NH$_2$ | OMe | OMe | 202–203 |
| 59 | 6a | Me | CO—c-N(CH$_2$)$_4$ | NHCONH—allyl | OMe | OMe | 205–206 (d) |
| 60 | 6a | Me | CON(Ph)$_2$ | NHCONH—allyl | OMe | OMe | 229–230 (d) |
| 61 | 6a | Me | CON(iPr)$_2$ | NHCONH—nBu | OMe | OMe | 218–219 |
| 62 | 6a | Me | CON(iPr)$_2$ | NHCONH—allyl | OMe | OMe | 220–221.5 |
| 63 | 4 | Me | SO$_2$N(Me)$_2$ | NH$_2$ | OMe | OMe | 187–189 (d) |
| 64 | 6a | Me | SO$_2$N(Me)$_2$ | NHCONH—nBu | OMe | OMe | 210–212 (d) |
| 65 | 6a | Me | SO$_2$N(Me)$_2$ | NHCONH—allyl | OMe | OMe | 203–205 (d) |
| 66 | 6b | Me | CON(Me)$_2$ | N(CONH—nBu)$_2$ | OMe | OMe | 145–146 |
| 67 | 6a | Me | CON(Me)$_2$ | NHCONH—allyl | OMe | OMe | 200–200.5 |
| 68 | 2 | Me | CON[(CH$_2$)$_2$]$_2$NCOOtBu | NO2 | OMe | OMe | 203–204 (d) |
| 69 | 2 | Me | CON[(CH$_2$)$_2$]$_2$NCOOtBu | NO$_2$ | OMe | OEt | 173–174 (d) |
| 70 | 9 | Me | CON[(CH$_2$)$_2$]$_2$NH | NO$_2$ | OMe | OMe | >300 (d) |
| 71 | 9 | Me | CON[(CH$_2$)$_2$]$_2$NH | NO$_2$ | OMe | OEt | >300 (d) |
| 72 | 2 | Me | SO$_2$—Ph-4-Me | NO$_2$ | OMe | OMe | 236–238 (d) |
| 73 | 2 | Me | CON(Et)$_2$ | NHCONH—nBu | R$_6$,R$_7$ = OCON(Et)$_2$ | | 85–87 |
| 74 | 6a | Me | CON(Et)$_2$ | NHCONH—allyl | OMe | OEt | 186–188 (d) |
| 75 | 6a | Me | CON[(CH$_2$)$_2$]$_2$NCOOtBu | NHCONH—allyl | OMe | OMe | 223–224 (d) |
| 76 | 6a | Me | CON[(CH$_2$)$_2$]$_2$NCOOtBu | NHCONH—nBu | OMe | OMe | 220–221 (d) |
| 77 | 2 | Me | CH$_2$OCOtBu | NO$_2$ | OMe | OMe | 152–154 |
| 78 | 6a | Me | SO$_2$Me | NHCONH—nBu | OMe | OMe | 196–198 (d) |
| 79 | 6a | Me | SO$_2$Me | NHCONH—allyl | OMe | OMe | 208–210 (d) |
| 80 | 9 | Me | CON[(CH$_2$)$_2$]$_2$NH | NHCONH—nBu | OMe | OMe | 185–186 (d) |
| 81 | 7b | Me | CON(Et)$_2$ | NHCO—nPentyl | OMe | OMe | 162–164 |
| 82 | 2 | Me | SO$_2$—Ph-4-Me | NH$_2$ | OMe | OMe | 172–174 (d) |
| 83 | 2 | Me | SO$_2$—Ph-4-Me | N(CONH—nBu)$_2$ | OMe | OMe | 115–118 |
| 84 | 1 | Me | CH$_2$Ph | NO$_2$ | OMe | OMe | 212–214 |

TABLE 2
Renal Vasodilating Activity

| Cmpd | Dose (mpk) | RBF | RVR | MABP | HR |
|---|---|---|---|---|---|
| 1 | 1.34 | +22 | 35 | −21 | +37 |
| 2 | 6.2 | +17 | −16 | −8 | −2 |
| 3 | 6.2 | +61 | −41 | −6 | +2 |
| 5 | 6.2 | +42 | −36 | −10 | +36 |
| 6 | 6.2 | +38 | −28 | −2 | −10 |
| 9 | 6.2 | +43 | −48 | −26 | 0 |
| 10 | 6.2 | +46 | −39 | −12 | +10 |
| 12 | 6.2 | +38 | −26 | — | +12 |
| 13 | 6.2 | +8 | −12 | −5 | +12 |
| 15 | 6.2 | +15 | −14 | −1 | +3 |
| 16 | 6.2 | +12 | −16 | −6 | +19 |
| 17 | 6.2 | +63 | −24 | +13 | −12 |
| 21 | 6.2 | +40 | −25 | +3 | +38 |
| 22 | 6.2 | +11 | −22 | −12 | +25 |
| 24 | 6.2 | +22 | −28 | −12 | +53 |
| 25 | 6.2 | +61 | −46 | −12 | +32 |
| 26 | 6.2 | +7 | −8 | 0 | 0 |
| 27 | 6.2 | +26 | −30 | −12 | +13 |
| 28 | 6.2 | +50 | −45 | −18 | +5 |
| 32 | 1.2 | +6 | −4 | +1 | −23 |
| 33 | 6.2 | +41 | −35 | −9 | −9 |
| 34 | 6.2 | +37 | −35 | −10 | +21 |
| 38 | 6.2 | +34 | −21 | +5 | −4 |
| 40 | 1.2 | +9 | −9 | −1 | — |
| 45 | 1.2 | +15 | −2 | +12 | +11 |
| 47 | 1.2 | +17 | −4 | +11 | −3 |
| 49 | 1.2 | +14 | −8 | +2 | −6 |
| 50 | 1.2 | +20 | −16 | 0 | −2 |

TABLE 2-continued

| | | Renal Vasodilating Activity | | | |
|---|---|---|---|---|---|
| Cmpd | Dose (mpk) | RBF | RVR | MABP | HR |
| 51 | 1.2 | +17 | −20 | −6 | +25 |
| 52 | 6.2 | +41 | −37 | −15 | 0 |
| 55 | 1.2 | +14 | −14 | −4 | +2 |
| 57 | 1.2 | +28 | −18 | +4 | +7 |
| 59 | 1.2 | +23 | −16 | +1 | +2 |
| 60 | 1.2 | +27 | −17 | +4 | +8 |
| 61 | 1.2 | +47 | −32 | −1 | +11 |
| 62 | 1.2 | +17 | −5 | +11 | 0 |
| 64 | 1.2 | +15 | −9 | +4 | 0 |
| 65 | 1.2 | +25 | −22 | −1 | −7 |
| 67 | 1.2 | +50 | −28 | +7 | 0 |
| 68 | 0.3 | +17 | −13 | −1 | +11 |
| 69 | 6.2 | +24 | −14 | +6 | +21 |
| 70 | 1.2 | +26 | −19 | −1 | +20 |
| 73 | 1.2 | +40 | −34 | −14 | −4 |
| 74 | 1.2 | +15 | −14 | −2 | −16 |
| 75 | 1.2 | +27 | −15 | +9 | +12 |
| 76 | 1.2 | +23 | −22 | −2 | −9 |
| 77 | 6.2 | +7 | −8 | −3 | +5 |
| 80 | 1.2 | +25 | −16 | 0 | +2 |
| 81 | 6.2 | +39 | −21 | +9 | −8 |

RBF is percent change in renal blood flow; RVR is percent change in renal vascular resistance; MABP is percent change in mean arterial blood pressure; HR is percent change in heart rate; all values are expressed as percent change relative to controls.

TABLE 3

| | | Cardiotonic Activity | | | |
|---|---|---|---|---|---|
| Cmpd | Dose (mpk, iv) | CF | dP/dt | HR | MABP |
| 4 | 0.375 | +100 | +46 | +7 | −25 |
| 7 | 0.875 | +59 | +34 | +4 | −10 |
| 8 | 0.375 | +124 | +54 | +10 | −20 |
| 10 | 1.87 | +70 | +91 | −6 | +18 |
| 11 | 1.87 | +126 | +47 | +25 | −17 |
| 12 | 1.87 | +70 | +51 | +14 | −10 |
| 13 | 1.87 | +49 | +24 | +6 | −8 |
| 22 | 1.87 | +43 | +68 | +2 | −23 |
| 23 | 1.87 | +27 | +24 | +5 | +3 |
| 25 | 1.87 | +49 | +61 | +5 | +12 |
| 27 | 1.87 | +87 | +41 | +46 | +17 |
| 28 | 0.875 | +71 | +70 | +27 | −4 |
| 29 | 1.87 | +79 | +58 | +13 | +6 |
| 33 | 1.87 | +132 | +84 | +18 | +17 |
| 36 | 1.87 | +26 | +26 | +9 | −1 |
| 39 | 1.87 | +76 | +73 | +16 | −1 |
| 41 | 1.87 | +166 | +62 | +29 | −34 |

CF is percent change in cardiac force; dP/dT is the maximum percent change in left ventricular pressure with time; MABP is percent change in mean arterial blood pressure; HR is percent change in heart rate; all values are expressed as percent change relative to controls.

TABLE 4

| Phosphodiesterase Fraction III Inhibitory Activity | |
|---|---|
| Cmpd | IC$_{50}$ (mM) |
| 3 | 6.0 |
| 9 | 100 |
| 10 | 45 |
| 11 | 30 |
| 18 | 225 |
| 19 | 42 |
| 21 | 14 |
| 22 | 3.5 |
| 26 | 20.5 |
| 34 | 35 |
| 43 | 34 |
| 44 | 180 |
| 63 | 185 |
| 70 | 78 |
| 71 | 22 |
| 74 | 115 |

METHODS OF PREPARING STARTING MATERIALS

The starting materials used to prepare the substituted isoquinolin-3-ol compounds of this invention can be prepared by one of the following general methods.

Method 1

In formula I when $R_6$ is an electron donating substituent, for example, a lower alkyl, lower alkoxy, halogen or acetamido radical, the compound can be prepared by either formylating (wherein $R_1$ is hydrogen) or acylating (wherein $R_1$ is lower alkyl or aryl) a phenyl compound of formula II wherein A is CN (phenylacetonitrile) or COOR [phenylacetic acid derivative in which R is hydrogen or lower alkyl] and $R_5$ to $R_8$ are

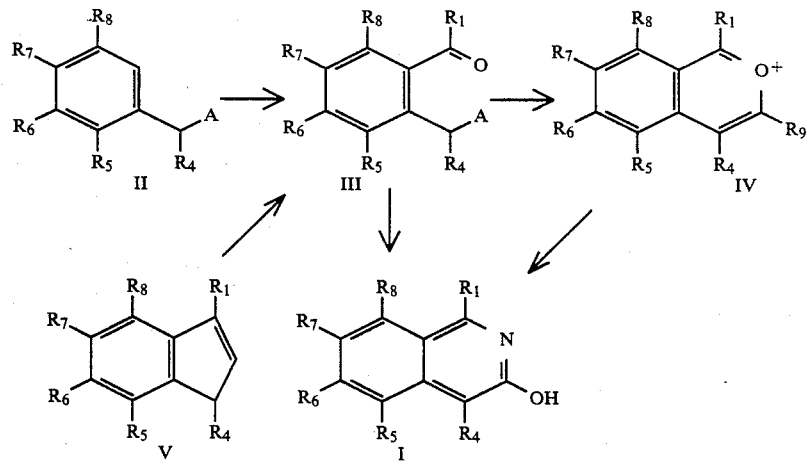

as already defined and $R_4$ is hydrogen, lower alkyl, aryl, acyl, or $(CHR)_n$-B wherein n is an integer from about 0 to about 10, B can be OR, COOR, or a halogen, wherein R is lower alkyl, substituted lower alkyl or aryl.

Formylation of II to give the o-formyl derivative III (wherein $R_1$ is hydrogen) can be performed by electrophilic substitution with HCN or metal cyanide salt and acid or with a formic acid derivative including, for examplee, $Cl_2CHOCH_3$, formamide, dimethylformamide and the like and a Lewis acid catalyst such as ZnCl₂, SnCl₄, AlCl₃, ZrCl₄, TiCl₄, BF₃ etherate, and the like. Acylation of II to provide O-acyl derivative III (where R₁ is lower alkyl or aryl) can be similarly effected under conventional Friedel-Crafts reaction conditions using either an acid chloride (R₁COCl), acid anhydride [(R₁CO)₂O] or an acid (R₁COOH) and a Lewis acid catalyst, such as including AlCl₃, ZrCl₄, TiCl₄, FeCl₃, ZnCl₂, SnCl₄, BF₃ etherate, HClO₄, (CF₃CO)₂O, CF₃SO₃H, or polyphosphoric acid (PPA). The o-acylphenylacetic acid derivative III can also be prepared by other methods such as oxidative ring opening of an appropriately substituted 1-indene derivative (V).

The o-formyl or o-acyl derivative III can either be directly converted to the isoquinoline derivative I upon reaction with ammonium hydroxide, ammonia or an acid salt thereof including ammonium acetate, ammonium carbonate and the like.

Alternatively, the o-formyl or o-acyl derivative III can be first treated with a strong acid including, for example, perchloric acid, trifluoroacetic acid, trifluorosulfonic acid, boron trifluoride etherate and the like to form a 2-benzopyrylium salt IV wherein R₉=OR (when A=COOR in II) or NHCOR₁ (when A=CN in II) having R and R₁ as described above. Treatment of the 2-benzopyrylium salt IV with ammonia or ammonium hydroxide in a solvent, for example, water, a lower alkanol such as ethanol, n-propanol or t-butanol, an ether such as diethyl ether or ethylene glycol diethyl ether, tetrahydrofuran (THF), a hydrocarbon such as benzene or toluene or a chlorohydrocarbon including methylene chloride, chloroform or carbon tetrachloride at zero degrees C. to about 150 degrees C. provides the isoquinolinol derivative I.

Method 2

3-Isoquinolinol compounds I wherein R₄ is halogen and the like preferably are prepared by electrophilic substitution at C₄ of I (wherein R₄ is hydrogen). Thus, for example, treating I with two equivalents of a halogen such as chlorine or bromine in acetic acid, chloroform, benzene and the like provides the hydrohalide (HX) salt of 4-halogenated derivative which upon neutralization with a base provides the 4-halogenated-3-isoquinolinol free base I (wherein R₄ is chloro or bromo). In the alternative, treatment with an appropriate N-halosuccinimide or similar reagent such as sulfuryl chloride or sulfuryl bromide (one equivalent) directly provides the 4-halogenated compound I (wherein R₄ is chloro, bromo or iodo).

Method 3

Isoquinolinol compounds of the general formula I containing R₇ as an electron releasing group and R₁–R₈ (as defined above) can be prepared by the Pomeranz-Fritsch type cyclization of an appropriately substituted intermediate (VI) with an acid such as sulfuric acid, PPA, BF₃ etherate and the like.

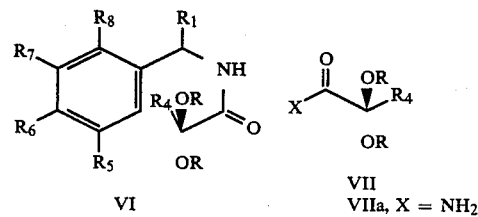

Compound VI can be prepared by reacting a benzylamine with acid derivative VII wherein X is halogen; OR and R are lower alkyl radicals and R₄ is as defined above. Alternatively, Compound VI can be prepared by displacing an appropriate benzyl halide by an amide anion derived from amide VIIa.

Method 4

Isoquinoline compounds I wherein R₄ is CN, COOR, CONH₂ or acyl can also be prepared by reacting o-acylhalobenzene VIII, wherein X is chloro, bromo or iodo, with a reactive methylene compound IX where P=CN, CONH₂ and R₄=CN, COR, COOR in the presence of a base including NaOR, NaH and NaNH₂ in solvents including ROH, RO(CH₂)OR, THF and benzene in the presence of a cuprous halide catalyst at about 60° C. to about 120° C. (wherein R is hydrogen, lower alkyl or aryl).

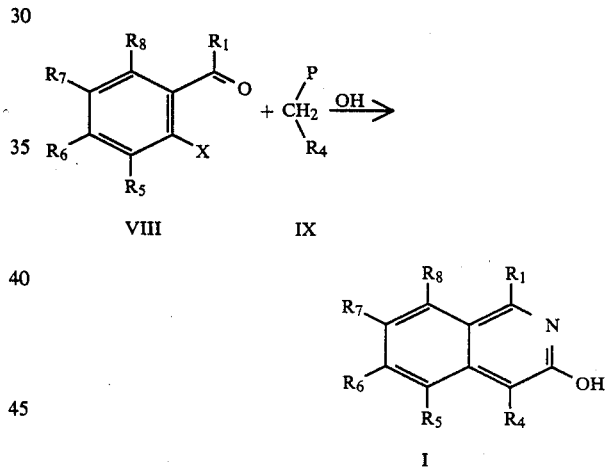

3-Isoquinolinol compounds I wherein R₄ is nitro or nitroso can be prepared by electrophilic substitution at C₄ of Formula I (wherein R₄ is H). In particular, treatment of Compound I with fuming nitric acid in acetic acid, acetic anhydride and the like alone or in combination with ether, methylene chloride and the like provides the 4-nitro derivative; and treatment with HNO₂ [generated by combining sodium nitrite and an acid or an alkylnitrite and an acid or base] provides the 4-nitroso derivative.

The 4-nitro or 4-nitroso derivative I can be reduced, for example, by hydrogenation to obtain the 4-amino derivative I (wherein R₄ is NH₂). If the hydrogenation is performed in the presence of an acid (such as acetic acid) and its anhydride (acetic anhydride), the corresponding 4-N-acylated derivative I (wherein R₄ is NHCOR) is provided.

Alternatively, the 4-amino derivative I (wherein R₄ is NH₂) can be treated with an acid chloride or an anhydride to provide 4-acylamino derivatives I (wherein R₄ is NHCOR and R is lower alkyl or aryl); with an inorganic cyanate (for example, NaOCN) in acidic medium (acetic acid) to provide the corresponding urea I (wherein $R_4$ is $NHCONH_2$); with an organic isocyanate to provide a substituted urea I (wherein $R_4$ is NHCONHR and R is lower alkyl or aryl); with an N,N-disubstituted carbamoyl chloride to provide an N,N-disubstituted urea I (wherein $R_4$ is $NHCON(R)_2$ and R is lower alkyl or aryl); or with a chloroformate to provide a carbamate I (wherein $R_4$ is NHCOOR and R is lower alkyl or aryl).

EXAMPLE A

4-β-Carbomethoxyethyl-3,6,7-trimethoxy-1-methyl-2-benzopyrylium Boron Trifluoride salt Boron trifluoride etherate (2.16 ml, 17.68 mmol) was slowly added to a stirred, cooled (in an ice bath) solution of 4.0 grams dimethyl 2-(3,4-dimethoxyphenyl) glutarate (13.49 mmol) in 6.43 ml acetic anhydride (67.49 mmol), and the mixture was stirred at room temperature for 48 hours. Upon dilution and stirring of the mixture with diethyl ether, 2.246 grams of Compound A was separated as a greenish-yellow solid (44% yield) having a melting point of 164°–167° C.

$^1$H NMR (CDCl$_3$): δ 2.62 (triplet, J=7 Hz, 2H, $CH_2COOCH_3$); δ 3.12 (singlet, 3H, 1-$CH_3$ eclipsing a multiplet of $CH_2CH_2COOCH_3$); δ 3.55 (singlet, 3H, $COOCH_3$); δ 4.00 (singlet, 3H, $OCH_3$); δ 4.13 (singlet, 3H, $OCH_3$); δ 4.37 (singlet, 3H, 3-$OCH_3$); δ 6.85 (singlet, 1H, ArH); δ 6.93 (singlet, 1H, ArH).

IR (KBr): 5.81, 6.15μ.

EXAMPLE B

4-β-Carbomethoxyethyl-3,6,7,8-tetramethoxy-1-methyl-2-benzopyrylium Perchlorate Boron trifluoride etherate (3.0 ml, 24.6 mmol) was slowly added to a solution of 4.0 grams dimethyl 2-(3,4,5-trimethoxyphenyl)glutarate (12.3 mmol) in 4.6 ml acetic anhydride (49 mmol). The solution was heated to 65° C. for 2.5 hours. The mixture was cooled (in an ice bath), and diluted with 180 ml diethyl ether. A 70% perchloric acid solution (17 ml) was added and a yellow percipitate was formed. The mixture was filtered to separate the precipitate which as then washed with diethyl ether and dried to provide 3.53 grams of Compound B (64% yield) having a melting point of 117°–119° C.

$^1$H NMR (CDCl$_3$): δ 2.63 (triplet, J=7 Hz, 2H, $CH_2CH_2COOCH_3$); δ 3.13 (triplet, J=7 Hz, $CH_2COOCH_3$); δ 3.22 (singlet, 3H, 1-$CH_3$); δ 3.63 (singlet, 3H, $COOCH_3$); δ 3.93 (singlet, 3H, $OCH_3$); δ 4.15 (singlet, 6H, $OCH_3$); δ 4.35 (singlet, 3H, $OCH_3$); δ 6.95 (singlet, 1H, Ar-H).

IR (KBr): 3.38, 5.75, 6.15μ.

EXAMPLE C

4-(β-Carbomethoxyethyl)-3-hydroxy-6,7-dimethoxy-1-methylisoquinoline

To an ice cooled and mechanically stirred slurry of 2.246 grams 4-β-carbomethxyethyl-3,6,7-trimethoxy-1-methyl-2-benzopyrylium boron trifluoride salt (5.95 mmol) in 2 ml water were added 60 ml concentrated ammonium hydroxide over a 10 minute period. The mixture was stirred for an additional 20 minutes. The yellow precipitate that formed was filtered, washed with water and dried to provide 1.07 grams of crude Compound C (59% yield). Recrystallization from ethanol provided 0.747 grams of pure Compound C having a melting point of 198°–200° C.

$^1$H NMR (CDCl$_3$): δ 2.65 (triplet, J=7 Hz, 2H, $CH_2CH_2COOCH_3$); δ 2.78 (singlet, 3H, 1-$CH_3$); δ 3.23 (multiplet, 2H, $CH_2COOCH_3$); δ 3.62 (singlet, 3H, $COOCH_3$); δ 3.92 (singlet, 3H, $OCH_3$); δ 4.00 (singlet, 3H, $OCH_3$); δ 6.82 (singlet, 1H, ArH); δ 6.92 (singlet, 1H, ArH).

IR (KBr): 5.81, 6.12, 6.39, 6.71μ.

Mass spectrum: m/e 305 (M+).

Anal. Calculated for $C_{16}H_{19}NO_5$: C, 62.94; H, 6.27; N, 4.59; Found: C, 62.63; H, 6.15; N, 4.62.

Use of the above procedure with the appropriately substituted 2-benzopyrylium salts (formula IV), principally as the perchlorate salts, provided a large number of 3-isoquinolinols (Formula I).

EXAMPLE D

3-Acetamido-7-ethoxy-6-methoxy-1-methyl-2-benzopyrylium Perchlorate

To an ice-cooled and stirred solution of 25 grams 4-ethoxy-3-methoxyphenylacetonitrile (0.13 mmol) in 74 ml acetic anhydride (0.785 mol) was slowly added perchloric acid (70%, 11.7N, 15.5 ml, 0.182 mol) over a 15 minute period. The dark reaction mixture slowly became a yellow slurry and was stirred at room temperature for 42 hours. The mixture was diluted with 200 ml diethyl ether and a crystalline yellow solid was isolated by filtration, washed with diethyl ether and dried in vacuo to provide 47.3 grams of Compound D (100% yield) having a melting point of 188°–189° C. (with decomposition).

$^1$H NMR (TFA): δ 1.62 (triplet, J=7 Hz, 3H, $OCH_2CH_3$); δ 2.53 (singlet, 3H, $3NHCOCH_3$); δ 3.22 (singlet, 3H, 1-$CH_3$); δ 4.28 (singlet, 3H, $OCH_3$); δ 4.42 (q, J=7 Hz, 2H, $OCH_2CH_3$); δ 7.40 (singlet, 1H, ArH); δ 7.48 (singlet, 1H, ArH); δ 8.37 (singlet, 1H, ArH).

IR (KBr): 5.88, 6.10, 6.23, 6.67μ.

Anal. Calculated for $C_{14}H_{18}ClNO_6$: C, 46.22; H, 4.99; N, 3.85; Cl, 9.75; Found: C, 46.42; H, 4.74; N, 3.82; Cl, 9.65.

EXAMPLE E

Dimethyl 2-(2-formyl-4,5-dimethoxyphenyl)glutarate

To a cold (ice-bath) solution of 10 grams dimethyl 2-(4,5-dimethoxyphenyl)glutarate (33.78 mmol) in 50 ml dry methylene chloride were added 9.0 grams aluminum chloride (67.57 mmol). Dichloromethyl methyl ether (7.77 grams, 67.57 mmol) was added dropwise to the cold solution over a 5 minute period. After the addition was complete, the mixture was stirred for 15 minutes in an ice bath, for 2 hours at room temperature and for an additional 30 minutes in the ice bath. The reaction mixture was poured over 50 ml concentrated hydrochloric acid and ice. The mixture was extracted with four successive 100 ml portions of methylene chloride, and the organic layer was washed with four successive 100 ml portions of water and two successive 100 ml portions of saturated sodium chloride solution and was dried over sodium sulfate. The methylene chloride was evaporated in vacuo to provide 11.48 grams of Compound E as an oil.

$^1$H NMR (CDCl$_3$): δ 2.01–2.50 (multiplet, 4H, $CH_2CH_2COOCH_3$); δ 3.62 (singlet, 3H, $COOCH_3$); δ 3.63 (singlet, 3H, $COOCH_3$); δ 3.92 (singlet, 6H, Ar-$OCH_3$); δ 6.85 (singlet, 1H, Ar-H); δ 7.30 (singlet, 1H, Ar-H); δ 10.2 (singlet, 1H, CHO).

IR (neat): 5.78, 5.95, 6.25 6.37, 6.62μ.
Mass spectrum: m/e 324 (M+).

EXAMPLE F

Dimethyl 2-(2-formyl-4,5-methylenedioxyphenyl)glutarate

To a cooled (ice bath) solution of 1.75 grams methyl 4,5-methylenedioxyphenylacetate (6.24 mmol) in 25 ml dry methylene chloride were added 0.832 grams aluminum chloride (6.24 mmol). Dichloromethyl methyl ether (1.44 grams, 12.47 mmol) was added dropwise to the cold solution over a five minute period. After the addition was complete, the mixture was stirred for 1 hour in an ice bath and for 4 hours at room temperature. The reaction mixture was quenched by pouring over 20 ml concentrated hydrochloric acid and ice, and the resulting solution was extracted with four successive 100 ml portions of methylene chloride. The organic layer was washed with five successive 100 ml portions of water and two successive 50 ml portions of a saturated sodium chloride solution, and dried over sodium sulfate. The methylene chloride was evaporated in vacuo to provide 2.11 grams of Compound F as an oily residue.

$^1$H NMR (CDCl$_3$): δ 2.10–2.46 (multiplet, 4H, CH$_2$CH$_2$COOCH$_3$); δ 2.8 (singlet, 3H, COOCH$_3$); δ 5.98 (singlet, 2H, OCH$_2$O); δ 6.82 (singlet, 1H, ArH); δ 7.20 (singlet, 1H, Ar-H); δ 10.13 (singlet, 1 H, CHO).

IR (neat): 3.67, 5.76, 5.92, 6.21, 6.73, 6.94μ.
Mass spectrum: m/e 308 (M+).

EXAMPLE G 4-(β-Carbomethoxyethyl)-3-hydroxy-6,7-dimethoxyisoquinoline

A mixture of 8.34 grams of dimethyl 2-(2-formyl-4,5-dimethoxyphenyl)glutarate (25.74 mmol), 17.86 grams anhydrous ammonium acetate (232 mmol) and 15 ml glacial acetic acid was heated to 75° C. and was maintained at that temperature for 30 minutes. After cooling, the yellow precipitate was isolated by filtration, washed with water and dried to provide 5.78 grams of Compound Q (77% yield). Recrystallization from methanol and trituration with ether (to remove any trace amounts of methanol) provided 4.57 grams of pure Compound G having a melting point of 178° to 180° C.

$^1$H NMR (CDCl$_3$): δ 2.68 (triplet, J=7 Hz, 2H, CH$_2$CH$_2$COOCH$_3$); δ 3.27 (triplet, J=7 Hz, 2H, CH$_2$COOCH$_3$); δ 3.63 (singlet, 3H, COOCH$_3$); δ 3.93 (singlet, 3H, OCH$_3$); δ 4.02 (singlet, 3H, OCH$_3$); δ 6.83 (singlet, 1H, ArH); δ 6.97 (singlet, 1H, ArH); δ 8.20 (singlet, 1H, 1-H); δ 13.4 (broad singlet, 1H, 3-OH).

IR (KBr): 5.75, 6.09, 6.33, 6.71μ.
Mass spectrum: m/e 291 (M+).
Anal. Calculated for C$_{15}$H$_{17}$NO$_5$: C, 61.85; H, 5.88; N, 4.81; Found: C, 61.88; H, 5.98; N, 4.63.

EXAMPLE H

3-Hydroxy-6,7-dimethoxy-1-methyl-4-nitroisoquinoline

3-Hydroxy-6,7-dimethoxy-1-methylisoquinoline (0.927 grams, 4.23 mmol) was dissolved in 60 ml glacial acetic acid by warming, and when the solution cooled to 15° C., a crystalline solid separated. To this mechanically stirred slurry were added 1.5 ml of a nitrating mixture (comprising 0.6 ml glacial acetic acid and 0.9 ml of 90 percent nitric acid) over a period of 15 minutes at 15° C. From the reaction mixture, a heavy yellow solid was isolated by filtration and washed with acetic acid. Alternatively, the reaction mixture was first quenched with 300 ml of water and the yellow solid was isolated by filtration, washed with water and dried in vacuo at 50° C. to provide 0.70 grams of Compound H (62.7% yield) having a melting point greater than 300° C.

$^1$H NMR (TFA): δ 3.23 (singlet, 3H, 1-CH$_3$); δ 4.20 (singlet, 3H, OCH$_3$); δ 4.32 (singlet, 3H, OCH$_3$); δ 7.65 (singlet, 1H, ArH); δ 8.70 (singlet, 1H, ArH).

Mass spectrum: m/e 264 (M+).
Anal. Calculated for C$_{12}$H$_{12}$N$_2$O$_5$: C, 54.55; H, 4.58; N, 10.60; Found: C, 54.24; H, 4.65; N, 10.32.

EXAMPLE I

4-Amino-3-hydroxy-6,7-dimethoxy-1-methylisoquinoline

3-Hydroxy-6,7-dimethoxy-1-methyl-4-nitroisoquinoline (16.0 grams, 60.54 mmol) was slurried in 600 ml glacial acetic acid and hydrogenated over 1.5 grams of a 10% palladium on carbon catalyst (Pd/C) at 17 psi hydrogen pressure at room temperature in a Parr hydrogenator for 1.5 hours. The reaction mixture was filtered through a Celite pad, and the filtrate was evaporated to dryness in vacuo to provide 20.48 grams of the diacetate solvate of the title compound as a dark greenish-yellow solid (95.6% yield) having a melting point of 111°–115° C.

$^1$H NMR (CDCl$_3$): δ 2.07 (singlet, 6H, CH$_3$COOH); δ 2.63 (singlet, 3H, 1-CH$_3$); δ 3.90 (singlet, 3H, OCH$_3$); δ 3.95 (singlet, 3H, OCH$_3$); δ 6.57 (singlet, 1H, ArH); δ 6.67 (singlet, 1H, ArH); δ 9.18 (broad singlet, 5H, NH$_2$, OH and CH$_3$COOH).

Mass spectrum: m/e 234 (M+ of free base).

To obtain the free base, the diacetate solvate (3.9 grams, 13.3 mmol) was treated with methanolic sodium methoxide (0.5M, 26.5 ml). The solid was collected, washed with methanol and then ether, and dried to provide 2.51 grams of the free base, melting point 250°–253° C.

$^1$H NMR (TFA): δ 3.10 (singlet, 3H, 1-CH$_3$), δ 4.16 (singlet, 3H, OCH$_3$), δ 4.23 (singlet, 3H, OCH$_3$), δ 7.36 (singlet, 1H, ArH), δ 7.50 (singlet, 1H, ArH).

IR(KBr): 3400, 1650, 1500, 1440, 1255 cm$^{-1}$.
Mass spectrum (DCI): 235 (M+1)+.
Anal. Calculated for C$_{18}$H$_{20}$N$_2$O$_5$: C, 61.52; H, 6.02; N, 11.96; Found: C, 61.41; H, 6.20; N, 11.64.

What is claimed is:

1. A compound of the formula:

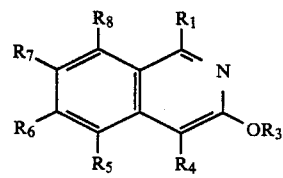

wherein R$_1$ is selected from the group consisting of hydrogen, lower alkyl, and halogen-substituted radicals thereof;

R$_3$ is selected from the group consisting of lower alkyl, amino lower alkyl, lower alkylamino lower alkyl, lower dialkylamino lower alkyl, cycloalkyl having 3–7 carbon atoms, alkenyl having 3–5 carbon atoms, alkynyl having 2–5 carbon atoms, and an acyl or sulfonyl radical of the formula Y(O)$_n$R wherein Y is a carbon atom or a sulfur atom and n is an integer having a value of 1 when Y is carbon and having a value of 2 when Y is sulfur, and R is hydrogen (except when Y is sulfur), lower alkyl, amino lower alkyl, lower alkylamino lower alkyl, lower dialkylamino lower alkyl, cycloalkyl having 3–7 carbon atoms, phenyl $C_{1-4}$-alkyl, naphthyl $C_{1-4}$-alkyl, phenyl, substituted phenyl wherein the substituent is methoxy or chloro, naphthyl, lower alkenyl having 3–5 carbon atoms, lower alkynyl having 2–5 carbon atoms, an amino radical of formula NR'R" wherein R' and R" are independently selected from hydrogen, lower alkyl, amino lower alkyl, lower alkylamino lower alkyl, lower dialkylamino lower alkyl, cycloalkyl having 3–7 carbon atoms, phenyl $C_{1-4}$ alkyl, naphthyl $C_{1-4}$ alkyl, phenyl, naphthyl, alkenyl having 3–5 carbon atoms and alkynyl having 2–5 carbon atoms, or R' and R" together with the nitrogen are a heterocyclic ring selected from morpholino, pyrrolidino, piperazino, piperidino, and azepino, or a substituted piperazino ring wherein the substituent is lower alkyl, lower alkoxy carbonyl, phenyl or substituted phenyl wherein the substituent is lower alkoxy, lower alkyl, nitro or halo, or a radical of formula OR''' wherein R''' may be lower alkyl, amino lower alkyl, lower alkylamino lower alkyl and lower dialkylamino lower alkyl, cycloalkyl having 3–7 carbon atoms, phenyl $C_{1-4}$ alkyl, naphthyl $C_{1-4}$ alkyl, phenyl, naphthyl, alkenyl having 3–5 carbon atoms or alkynyl having 2–5 carbon atoms; and $R_4$ is selected from the group consisting of nitro, nitroso, an amino radical of the formula NR'R" wherein R' and R" are as defined above, N(COR')$_2$ wherein R' is as defined above, COR' or COOR' wherein R' is as defined above, CONR'R" wherein R' and R" independently are as defined above, —(CH$_2$)$_x$—Z wherein x is an integer from 1 to 8, and Z is cyano, OR', OCOR', COOR', or CONR'R" wherein R' and R" independently are as defined above, N(CONHR')$_2$ wherein R' is as defined above, NHCO(Q)(R')$_p$ wherein Q is oxygen or N(H)$_m$ and R' is as defined above, with the proviso that when Q is oxygen, R' is other than hydrogen and p is 1, and that when Q is N(H)$_m$, m and p independently may be zero, 1, or 2 provided that the sum of m and p is 2;

$R_5$, $R_6$, $R_7$, and $R_8$ may be independently selected from the group consisting of hydrogen, halogen, hydroxy, acyloxy, carbamyloxy, lower alkylcarbamyloxy and lower alkoxy; and $R_5$ and $R_6$, $R_6$ and $R_7$ or $R_8$ when taken together may form a methylenedioxy ring.

2. The compound of claim 1 wherein $R_1$ is lower alkyl or halo lower alkyl; $R_3$ is lower alkyl, phenyl $C_{1-4}$-alkyl, naphthyl $C_{1-4}$-alkyl, or Y(O)$_n$R; $R_4$ is nitro, N(COR')$_2$, N(CONHR')$_2$, COOR', NR'R"; NR"COR' or NHCO(Q)(R)$_p$; $R_5$ and $R_8$ are hydrogen; and $R_6$ and $R_7$ are lower alkoxy, carbamyloxy or hydrogen.

3. The compound of claim 1 which compound is 3-acetoxy-7-ethoxy-6-methoxy-1-methyl-4-nitroisoquinoline.

4. The compound of claim 1 which compound is 3-dimethylcarbamyloxy-7-ethoxy-6-methoxy-1-methyl-4-nitroisoquinoline.

5. The compound of claim 1 which compound is 4-[N'-(allylureido)]-3-dimethylcarbamyloxy-6,7-dimethoxy-1-methyliosquinoline.

6. The compound of claim 1 which compound is 6,7-dimethoxy-1-methyl-4-[N-(propanamido)]-3-propanoyloxyisoquinoline.

7. The compound of claim 1 which compound is 4-[N'-(n-butylureido)]-3-diethylcarbamyloxy-6,7-dimethoxy-1-methylisoquinoline.

8. A compound of claim 1 selected from the group consisting of 3-acetoxy-7-n-butoxy-6-methoxy-1-methyl-4-nitroisoquinoline; 7-ethoxy-6-methoxy-1-methyl-3-propanoyloxy-4-nitroisoquinoline; 3-benzoyloxy-7-ethoxy-6-methoxy-1-methyl-4-nitroisoquinoline; 7-ethoxy-6-methoxy-3-(4-methoxybenzoyloxy)-1-methyl-4-nitroisoquinoline; 3-butanoyloxy-6,7-dimethoxy-1-methyl-4-nitroisoquinoline; 4-[N'-(n-butylureido)]-3-diisopropylcarbamyloxy-6,7-dimethoxy-1-methylisoquinoline; 4-[N'-(n-butylureido)]-3,6,7-tri(diethylcarbamyloxy)-1-methylisoquinoline; 3-[4-(t-butoxycarbonyl)piperazin-1-yl-carbonyloxy]-6,7-dimethoxy-1-methyl-4-nitroisoquinoline.

9. A pharmaceutical composition comprising an effective amount of a compound according to claim 1 as the active ingredient dispersed in a pharmaceutically acceptable carrier.

10. The pharmaceutical composition according to claim 9 wherein said compound is capable of increasing the efficiency of cardiac contractions in the amount present in the composition when said composition is introduced into a mammal.

11. The pharmaceutical composition according to claim 9 wherein said compound is capable of increasing the contractile force of cardiac muscle in the amount present in the composition when said composition is introduced into a mammal.

12. The pharmaceutical composition according to claim 9 wherein said compound is capable of stimulating renal vasodilation in the amount present in the composition when said composition is introduced into a mammal.

13. The pharmaceutical composition according to claim 9 wherein said compound is capable of inhibiting the hydrolytic activity of phosphodiesterase fraction III in the amount present in the composition when said composition is introduced into a mammal.

14. A method for increasing the contractile force of cardiac muscle in a mammal comprising administering to said mammal a unit dose of the pharmaceutical composition according to claim 9.

15. A method for stimulating vasodilation in a mammal comprising administering to said mammal a unit dose of the pharmaceutical composition according to claim 9.

* * * * *